(12) United States Patent
Hill et al.

(10) Patent No.: US 7,741,063 B2
(45) Date of Patent: Jun. 22, 2010

(54) TOXOPLASMA GONDII OOCYST PROTEIN

(75) Inventors: Dolores Hill, Hague, VA (US); Dante S Zarlenga, Ellicott City, MD (US); Cathleen Coss, Catonsville, MD (US); Jitender P Dubey, Greenbelt, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/436,596

(22) Filed: May 6, 2009

(65) Prior Publication Data

US 2009/0215696 A1    Aug. 27, 2009

Related U.S. Application Data

(62) Division of application No. 11/701,872, filed on Feb. 2, 2007, now Pat. No. 7,544,789.

(51) Int. Cl.
*G01N 33/53* (2006.01)
*C07K 14/45* (2006.01)
*C12N 15/63* (2006.01)

(52) U.S. Cl. .................. 435/7.1; 530/350; 435/69.7
(58) Field of Classification Search .................. None
See application file for complete search history.

(56) References Cited

OTHER PUBLICATIONS

Lecordier, Laurence et al., "Molecular structure of *Toxoplasma gondii* dense granule antigen(GRA 5) associated with the parasitophorous vacuole membrane," Molecular and Biochemical Parasitology, 1993, vol. 59, pp. 143-153.
Gamble, H. Ray et al., "Use of Recombinant Antigens for Detection of *Toxoplasma gondii* Infection in Swine," The Journal of Parasitology, Jun. 2000, vol. 86, No. 3, pp. 459-462.
NCCLS, "Clinical Use and Interpretation of Serologic Tests for Toxoplasma gondii; Approved Guideline," M36-A, vol. 24, No. 6.

*Primary Examiner*—Prema Mertz
(74) *Attorney, Agent, or Firm*—John D. Fado; G. Byron Stover

(57) ABSTRACT

Recombinant proteins have been developed for the detection of *Toxoplasma gondii* oocyst proteins for example in biological fluids. Isolated DNA sequences which encode these proteins have also been developed. The DNA sequences may be inserted into recombinant DNA molecules such as cloning vectors or expression vectors for the transformation of cells and the production of the proteins.

9 Claims, 3 Drawing Sheets

TOXOPLASMA GONDII OOCYST PROTEIN

This is a divisional of application Ser. No. 11/701,872 filed Feb. 2, 2007, which is herein incorporated by reference in its entirety.

BACKGROUND OF THE INVENTION

The present invention relates to an isolated 18.3 kDa protein, DGP5p+, specific for *Toxoplasma gondii*, which contains a transmembrane protein. The present invention also relates to DGP5p protein which lacks the transmembrane protein of DGP5p+; recombinant DGP5p (rDGP5p) protein; and the nucleic acid sequences which encode these proteins. The RNA which encodes DGP5p and rDGP5p can be used to specifically identify *T. gondii* oocysts through RT-PCR. The isolated and recombinant proteins can be used as reagents to detect antibodies in the serum of infected individuals.

Toxoplasmosis, caused by the protozoan parasite *Toxoplasma gondii*, is one of the most common parasitic infections of man and other warm-blooded animals. It has been found worldwide from Alaska to Australia. Nearly one-third of humanity has been exposed to this parasite. in most adults it does not cause serious illness, but it can cause blindness and mental retardation in congenitally infected children and devastating disease in immunocompromised individuals (Dubey, J. P., and T. P. Beattie, Toxoplasmosis of animals and man, CRC Press, Boca Raton, Fla., 1988). Humans become infected by congenital transmission from mother to fetus, through ingestion of tissue cysts in under-cooked or uncooked meat, or by ingesting food or water contaminated with sporulated oocysts from infected feces (e.g., cat). Food animals, such as pigs, become infected by the same routes, resulting in meat products containing tissue cysts which could infect consumers. Currently, there are no tests which can differentiate between oocyst ingestion versus tissue cyst ingestion as the infection route. Development of such a test would make epidemiological studies possible to determine predominant infection routes, could lead to the development of fact-based strategies to reduce transmission, and could increase public perception of pork as a safe food product. Increased consumer awareness of the potential risks of acquiring *T. gondii* from fresh pork products represents a potentially serious problem for the U.S. pork industry. Food safety is a critical issue for the swine industry. Foodborne diseases are increasing in industrialized countries and consequently are more of a concern to consumers. Large outbreaks of foodborne diseases are being reported and covered extensively in the media, and the severe impact on children, the aged, and immunocompromised individuals has resulted in a heightened awareness of the consumer to the issue of contaminated food. Demands of consumers for pathogen free meat products have focused attention of government regulators and the meat industry on food safety, and the necessity to produce meat that is wholesome, safe and of high quality. Delivery of a safe product is essential for pork to remain a competitive commodity, both in the U.S. and globally.

Thus, there is a need for an agent useful for differentiating between oocyst versus tissue cyst induced *T. gondii* infection in humans and food animals.

SUMMARY OF THE INVENTION

We have identified *T. gondii* oocyst protein-specific antigens. Isolated and recombinant *T. gondii*-specific proteins can be used in a number of different ways. First, the recombinant antigens can be adsorbed to the surface of microtiter plates or to immunoblotting membrane and used in an ELISA format for detection of antibodies in serum of patients exhibiting clinical signs of toxoplasmosis. Second, the recombinant antigens can be used to prepare monoclonal antibodies (mAb) which selectively identify or which are specific for *T. gondii* oocyst proteins. These mAbs can be used in ELISA and in IFA to detect the parasite in biological samples or in water samples. Third, primers directed to *T. gondii*-specific regions of the DNA sequences can be produced for sensitive detection of the parasite by polymerase chain reaction (PCR), primers can be used in RT-PCR to specifically identify transcription of *T. gondii*-specific proteins.

We have now discovered novel recombinant DNA clones which encode oocyst proteins of *T. gondii*, which may have immunodiagnostic potential for toxoplasmosis. The DNA sequences may be inserted into DNA molecules such as cloning vectors or expression vectors for the transformation of cells and the production of the *T. gondii*-specific proteins.

In accordance with this discovery, it is an object of the invention to provide new proteins and peptides, comprising all or part of the amino acid sequences shown in SEQ ID NO:1, that are specific for *T. gondii* and that can bind antibodies specific for *T. gondii* and/or elicit an immune response specific for *T. gondii*. This invention, in addition to the above, also encompasses a method of identifying *T. gondii* oocyst infection of a subject, comprising: contacting a body fluid obtained from the subject with the peptide of this invention and detecting any selective binding of the peptide to any anti-*T. gondii* oocyst antibodies in the body fluid.

It is also an object of the invention to provide new proteins and peptides that are specific for *T. gondii* and that can therefore be used to generate antibodies for identifying the presence of *T. gondii* oocysts in biological samples and in water. It is part of this invention to provide the genes which encode these peptides.

In particular, this invention comprises a method of diagnosing *T. gondii* oocyst infection of a subject, comprising contacting a body substance obtained from the subject with an anti-*T. gondii* oocyst antibody; and detecting any selective binding of the antibody to any antigenic *T. gondii*-oocyst specific peptide present in the body substance.

It is also an object of the invention to provide new proteins and peptides that are specific for *T. gondii* and that can therefore be used to generate monoclonal or polyclonal antibodies. It is part of this invention to provide the genes which encode these peptides.

Further, the invention can comprise fusion proteins comprising one of the peptides described above comprising one or more epitopes of rDGP5p protein wherein said rDGP5p protein comprises an amino acid sequence shown in SEQ ID NO:1 and wherein said protein is antigenic and effective to elicit an immune response against *T. gondii* oocysts in a host animal and a second unrelated peptide expressed by a regulatory DNA segment operably coupled to the DNA segment described herein (SEQ ID NO:2) that encodes the peptide of this invention. In addition, the invention can comprise fusion proteins comprising the unrelated peptide expressed by a regulatory DNA segment operably coupled to a DNA nucleotide sequence encoding a fusion protein comprising one of the peptides described above comprising one or more epitopes of rDGP5p protein wherein said rDGP5p protein comprises an amino acid sequence shown in SEQ ID NO:1. It is part of this invention to provide the genes which encode these fusion proteins. Still part of this invention are fusion RNA and DNA polymers comprising the RNA or DNA of this invention and a second unrelated polyRNA or polyDNA segment.

Additionally, it is an object of the invention to provide DNA primers from the sequence described in SEQ ID NO:2. The invention further comprises a method for specifically identifying *T. gondii* oocysts which comprises amplifying a subject mRNA by the RT-PCR method with the use of the above-mentioned DNA primers and thus assaying the expression of the DGP5p gene.

Also part of this invention is a *T. gondii* oocyst diagnostic kit, comprising anti-*T. gondii*-oocyst specific antibodies; and instructions for the use of the kit.

Furthermore, this invention also provides a *T. gondii* oocyst diagnostic kit, comprising the proteins and peptides of this invention; and instructions for use of the kit.

Other objects and advantages of this invention will become readily apparent from the ensuing description.

DETAILED DESCRIPTION OF THE INVENTION

Figure 1:
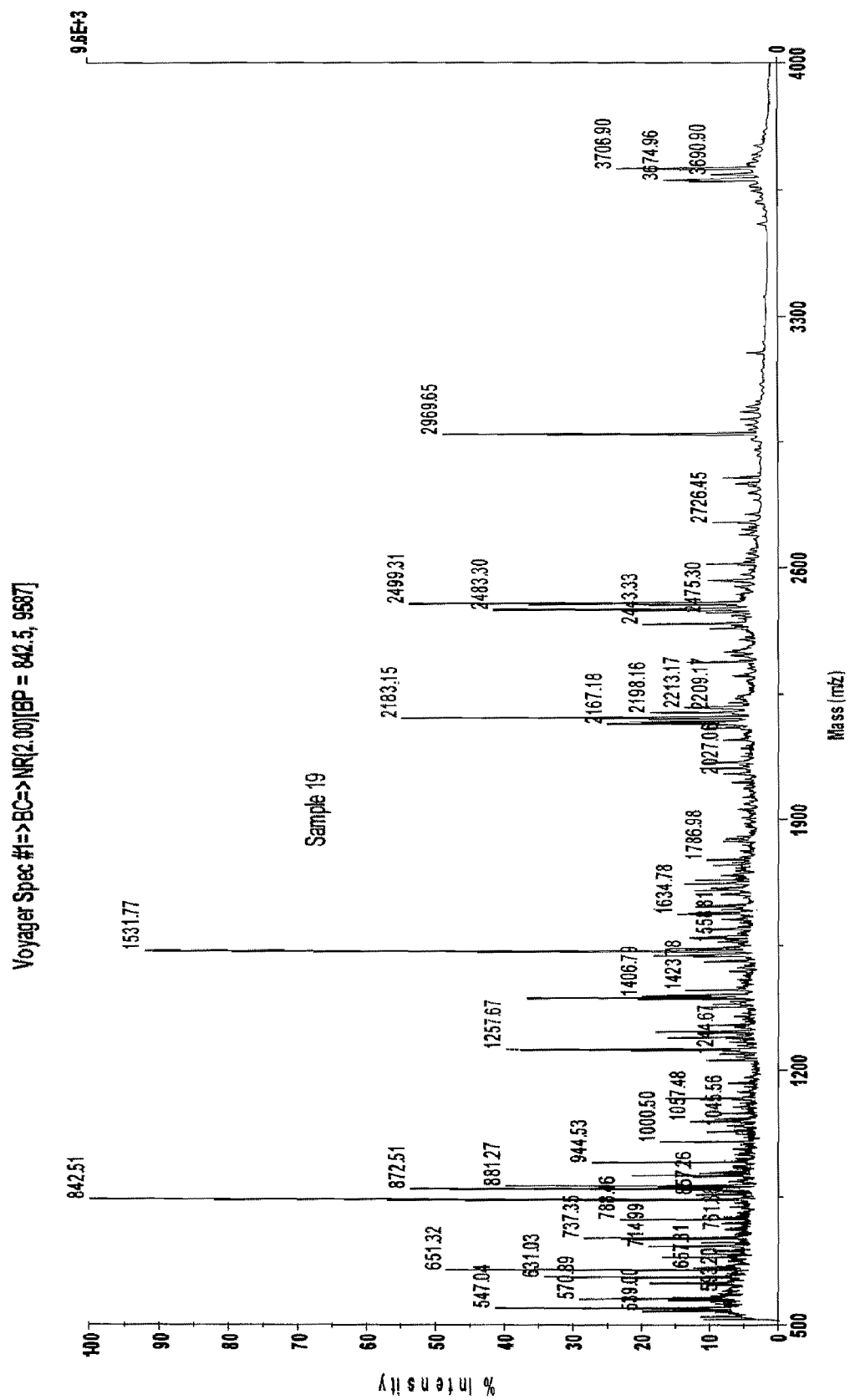
FIG. 1 shows the Matrix assisted laser desorption/ionization time of flight spectra (MALDI-TOF) of peptide masses resulting from digestion of DGP5p+ excised 2-dimensional gel spot (described below).

We have identified an oocyst specific 18.3 kDa protein (DGP5p+) and validated assays (e.g., recombinant-based ELISA serological assay) that can differentiate between oocyst versus tissue cyst induced *T. gondii* infection in humans and food animals. The native 18.3 kDa DGP5p+ protein was typically isolated from the organism with a 5 kDa transmembrane protein attached which permits transport across the dense granule membrane. The recombinant protein rDGP5p does not contain this transmembrane unit and was expressed as a 13 kDa protein.

The present invention provides an isolated 18.3 kDa protein, DGP5p+, and recombinant protein rDGP5p (13 kDa), all of which are specific for *Toxoplasma gondii* oocysts, and the nucleic acid sequences that encode rDGP5p. Antibodies resulting from immunizations with the recombinant 13 kDa proteins specifically bind the native 18.3 kDa protein, DGP5p+ (and also rDGP5p), which is specific for *T. gondii* oocysts. Antibodies resulting from immunizations with the native 18.3 kDa protein specifically bind rDGP5p, which is specific for *T. gondii* oocysts. The invention encompasses a recombinant bacteriophage clone, designated rDGP5p, comprising a nucleotide sequence (SEQ ID No. 2) encoding rDGP5p recombinant proteins. The predicted amino acid sequence (SEQ ID NO:1) of rDGP5p (i.e., the 13 kDa protein) is shown below; the invention encompasses DNA sequences which encode peptides having amino acid sequences that are homologous to that of rDGP5p. "Homologous" peptides are defined herein as peptides having an amino acid sequence sufficiently duplicative of rDGP5p proteins to be antigenic and capable of eliciting antibody which specifically and selectively bind to *T. gondii* oocysts DNA sequences encoding rDGP5p proteins with the amino acid sequence (SEQ ID NO:1)-shown below and DNA sequences which encode homologous proteins and which also hybridize to the DNA sequence encoding rDGP5p proteins (or its complement) under stringent conditions are particularly preferred.

Further, because of the degeneracy of the genetic code, there exists a finite set of nucleotide sequences which can code for a given amino acid sequence. It is understood that all such equivalent sequences are operable variants of the disclosed sequence, since all give rise to the same protein (i.e., the same amino acid sequence) during in vivo transcription and translation, and are hence encompassed by the instant invention. DNA sequences which are substantially homologous to the nucleotide sequence encoding rDGP5p proteins are also encompassed by the invention. As defined herein, two DNA sequences are substantially homologous when at least 85% (preferably at least 90% and most preferably 95%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., 1989, Molecular Cloning: A Laboratory Manual, Cold Spring Harbor Laboratory, Cold Spring, N.Y., or DNA Cloning: A Practical Approach, Vol. I and II (Ed. D. N. Glover), IRL Press, Oxford, 1985. Sambrook et al. describe highly stringent conditions as a hybridization temperature 5-10° C. below the $T_m$ of a perfectly matched target and probe; thus, sequences that are "substantially homologous" would hybridize under such conditions.

The present invention also encompasses rDGP5p variants. A preferred rDGP5p variant is one having at least 80% amino acid sequence similarity to the rDGP5p amino acid sequence (SEQ ID NO:1), a more preferred rDGP5p variant is one having at least 90% amino acid sequence similarity to SEQ ID NO:1 and a most preferred rDGP5p variant is one having at least 95% amino acid sequence similarity to SEQ ID NO:1 as defined by the algorithm, CLUSTRAL or PILEUP.

A "variant" of rDGP5p may have an amino acid sequence that is different by one or more amino acid "substitutions". The variant may have "conservative substitutions", wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software. The term "biological activity" refers to rDGP5p having structural, regulatory or biochemical functions of the naturally occurring protein. Likewise, "immunological activity" defines the capability of the natural, recombinant or synthetic rDGP5p, or any oligopeptide thereof, to induce a specific immune response in appropriate animals or cells and to bind with specific antibodies.

The phrase "conservative substitution" also includes the use of a chemically derivatized residue in place of a non-derivatized residue. "Chemical derivative" refers to the chemical modification of a nucleic acid sequence encoding rDGP5p or the encoded rDGP5p wherein the subject nucleic acid or polypeptide has one or more residues chemically derivatized by reaction of a functional side group. Examples of such modifications would be replacement of hydrogen by an alkyl, acyl, or amino group; however, replacements are not limited to these groups. A nucleic acid derivative would encode a polypeptide which retains essential biological characteristics of natural rDGP5p. Also included are those peptides which contain one or more naturally-occurring amino acid derivatives of the twenty standard amino acids, e.g., 5-hydroxylysine or ornithine may be substituted for lysine.

The term "peptide" as used herein refers to a molecular chain of amino acids with a biological activity (e.g., capable of binding antibody specific for *T. gondii* oocysts), and does not refer to a specific length of the product. Thus, inter alia, proteins, oligopeptides, polypeptides and fusion proteins as well as fusion peptides are included. Further, DGP5p+ and rDGP5p are interchangeable as reagents for detecting *T. gondii*-oocyst specific antibodies, for generating *T. gondii*-oocyst specific antibodies, and for vaccine development. Thus, inter alia, reference to DGP5p+ encompasses rDGP5p, and reference to rDGP5p encompasses DGP5p+.

The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, humanized, CDR-grafted, and single chain antibodies, and the like. Fragments of immunoglobulins, including Fab fragments and fragments produced by an expression library, including phage display. See, e.g., Paul, Fundamental Immunology, Third Ed., 1993, Raven Press, New York, for antibody structure and terminology.

The phrases "specifically binds to" or "specifically immunoreactive with", when referring to an antibody or other binding moiety refers to a binding reaction which is determinative of the presence of the target analyte in the presence of a heterogeneous population of proteins and other biologics. Thus, under designated assay conditions, the specified binding moieties bind preferentially to a particular target analyte and do not bind in a significant amount to other components present in a test sample. Specific binding to a target analyte under such conditions may require a binding moiety that is selected for its specificity for a particular target analyte. A variety of immunoassay formats may be used to select antibodies specifically immunoreactive with a particular protein. For example, solid-phase ELISA immunoassays are routinely used to select monoclonal antibodies specifically immunoreactive with an analyte. See Harlow and Lane (1988), Antibodies, A Laboratory Manual, Cold Spring Harbor Publications, New York, for a description of immunoassay formats and conditions that can be used to determine specific immuno-reactivity. Typically a specific or selective reaction will be at least twice background signal to noise and more typically more-than 10 to 100 times background.

The DNA sequences of the invention can be used to prepare recombinant DNA molecules by cloning in any suitable vector. A variety of vector-host combinations may be employed in practicing the present invention. Host cells may be either prokaryotic or eukaryotic, and, when the host cells are bacterial cells, they may be either gram-negative or grain-positive bacteria. Without being limited thereto, examples of hosts suitable for use herein are prokaryotic and eukaryotic hosts such as *E. coli* K12 or XL1Blue cells and related bacteria, *Saccharomyces cerevisiae*, Sf9 or Sf21 insect cells (*Spodoptera frugiperda*), Chinese hamster ovary cells, and plant cells in culture. However, other hosts may also be utilized.

Vectors used in practicing the present invention are selected to be operable as cloning vectors or expression vectors in the selected host cell. Numerous vectors are known to those of skill in the art, and selection of an appropriate vector and host cell is a matter of choice. This invention encompasses a hybrid vector, that comprises a vector capable of replication, transcription and expression of DNA segments operably coupled thereto; and a DNA segment encoding a polypeptide of this invention comprising the peptide disclosed herein operatively coupled thereto, wherein when the vector is placed in an appropriate host it can express the polypeptide encoded by the DNA segment. Examples of such vectors are pGex (Pharmacia), baculovirus, pET-9d (Novagen), pRSET T7 (Invitrogen), pTriplEx2 plasmid vector and pMal-c2 plasmid vector (Invitrogen). Vectors actually used below were pTriplEx2 plasmid vector and pMal-c2 plasmid vector. However, other vectors may also be utilized. The vector may be a eukaryotic or a prokaryotic vector depending on the host selected for transfection and in which the gene product is going to be expressed.

Still part of this invention is another hybrid vector, that comprises a vector capable of replication, transcription and expression of DNA segments operably coupled thereto; and a DNA segment comprising a DNA fragment encoding at least one of the polypeptides of the invention and a second unrelated DNA segment, both sequences being operably coupled to one another and to the vector. The preparation of the hybrid vector described above is known in the art and need not be further described herein (Smith, D., and K. Johnson, "Single Step Purification of Polypeptides Expressed in *E. coli* as Fusions with Glutathione S-transferase", Gene, 67:31(1988); Studier, F. W., et al., "Use of T7 RNA Polymerase to Direct Expression of Cloned Genes", Meth. Enzymol., 185:60-89 (1990)).

The vectors may, for example, be bacteriophages, plasmids, viruses, or hybrids thereof. A number of prokaryotic expression vectors are described in U.S. Pat. Nos. 4,652,525, 4,440,859, 4,436,815, and 4,342,832, and a number of eukaryotic expression vectors have also been described in U.S. Pat. Nos. 4,546,082, 4,510,245, and 4,446,235. Further, the vectors may be non-fusion vectors (i.e., those producing the antigenic protein of the invention not fused to any heterologous polypeptide), or alternatively, fusion vector (i.e., those producing the antigenic protein fused to a vector encoded polypeptide). The fusion proteins would of course vary with the particular vector chosen. Suitable non-fusion plasmid vectors for use with *E. coli* include, but are not limited to, pTrc99 for use with *E. coli* JM 105, or pANK-12, pANH-1 or pPL2 for use with *E. coli* MZ 1. Conversely, suitable fusion plasmid vectors include pGEX and pMC1871 for use with *E. coli* JM 105, pMAL with *E. coli* PR 722, pVB2 with *E. coli* LA5709, pTrcHis with *E. coli* INV F' and DH5, pCO5 with *E. coli* N6405, and pRIT2T or pEZZ 18 with *E. coli* N4830-1. Other, non-*E. coli* expression systems which may also be employed include pAc360 or pBluescript for use with SP2 or High 5 insect cells, pYesHis with the yeast *T. cerevisiae* INVSc1 or INVSc2, pLS405 with *Salmonella dublin* SL598, and pYUB12 with *Mycobacterium smegmatis* or *M. bovis*. Still other suitable vector-host combinations that may be used in practicing the instant invention are described, for example, in U.S. Pat. No. 5,122,471.

Within each specific vector, various sites may be selected for insertion of the isolated DNA sequence. These sites are usually designated by the restriction enzyme or endonuclease that cuts them. For example, in pBR322, the Pst I site is located in the gene for penicillinase between the nucleotide triplets that code for amino acids 181 and 182 of the penicillinase protein.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

The DNA sequences of the invention may be inserted into the desired vector by known techniques. If, however, the vector is to serve as an expression vector, the vector should have a promoter, and the DNA sequence should be inserted in the vector downstream of the promoter and operationally associated therewith. While control sequences may be ligated to the coding sequence prior to insertion into the vector, preferably, the vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be.

The antigenic peptides of the invention are produced by growing host cells transformed by the expression vectors described above under conditions whereby the antigen is produced. The antigens are then isolated from the host cells. The selection of the appropriate growth conditions and recovery methods are well within the skill of the art. A recombinant DGP5p protein has been produced in the pMal-c2 plasmid vector expression system. The recombinant DGP5p antigen is produced as an N-terminal maltose binding fusion protein under the control of the lac repressor.

Labeled oligonucleotide probes may be readily prepared using techniques known in the art, such as automated synthesis, using the nucleotide sequence encoding rDGP5p disclosed herein. The particular nucleotide sequences selected are chosen so as to correspond to codons encoding an amino acid sequence of the antigen. While the exact length of the probe is not critical, it is generally recognized that probes from about 15 to about 20 base pairs are usually effective. Greater selectivity may be achieved using longer probes. The probes may be labeled with a marker, such as a radionucleotide or biotin using standard procedures, and used to screen the libraries by Southern hybridization. Procedures for the hybridization assay are described, for example, in U.S. Pat. No. 5,041,378, and in Nucleic Acid Hybridization, (Ed. Hames and Higgins) 1985. Once a clone from the screened library has been identified by positive hybridization,: it can be confirmed by methods such as restriction enzyme analysis and DNA sequencing that the clone contains a gene that encodes the amino acid sequence comprising all or part of SEQ ID NO:1 or a homologous amino acid sequence.

For RT-PCR, mRNA is transcribed into cDNA using a gene specific primer (or oligo dT if the gene sequence is unknown) and reverse transcriptase. After the first strand cDNA is produced (the RT reaction), the second DNA strand is generated using an upstream gene specific primer. This second reaction, i.e., the PCR part, with downstream and upstream primers is repeated 25-35 times to produce a DNA fragment originating from the mRNA.

The peptides and proteins of this invention can be used as immunogens to generate antibodies that are selectively specific for proteins contained within T. gondii oocystes. Thus, rDGP5p can be used to generate monoclonal and polyclonal antibodies and hyperimmune serum and hyperimmune colostrum.

To prepare antibodies, a host animal is immunized using the DGP5p protein as the immunogen. The host serum or plasma is collected following an appropriate time interval to provide a composition comprising antibodies reactive with the immunogen. Methods of antibody (polyclonal and monoclonal) production and isolation are well known in the art. See, for example, Harlow et al., 1988, supra. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-antibody.

In another embodiment, the monoclonal antibody of the invention is a chimeric monoclonal antibody or a humanized monoclonal antibody, produced by techniques well-known in the art.

The peptides and proteins of this invention can be used as immunogens in vaccines for vaccination against T. gondii. The vaccines can be used to prevent or reduce susceptibility to disease caused by T. gondii. While the peptides are effective for eliciting antibody production in a variety of animals, the peptides are particularly preferred for the treatment of bovine or porcine animals.

The peptides and proteins of this invention can be formulated as univalent and multivalent vaccines. The rDGP5p peptide can be used as produced or isolated by the methods described above. The protein can be mixed, conjugated or fused with other antigens, including B or T cell epitopes of other antigens. In addition to its utility as a primary immunogen, the rDGP5p peptide can be used as a carrier protein to confer or enhance immunogenicity of other antigens.

When a haptenic peptide of protein rDGP5p is used, (i.e., a peptide which reacts with anti-DGP5p specific antibodies, but cannot itself elicit an immune response), it can be conjugated to an immunogenic carrier molecule. For example, an oligopeptide containing one or more epitopes of rDGP5p protein may be haptenic. Conjugation to an immunogenic carrier can render the oligopeptide immunogenic. Preferred carrier proteins for the haptenic peptides of rDGP5p are tetanus toxin or toxoid, diphtheria toxin or toxoid and any mutant forms of these proteins such as CRM 197. Others include exotoxin A of *Pseudomonas*, heat labile toxin of *E. coli* and rotaviral particles (including rotavirus and VP6 particles). Alternatively, a fragment or epitope of the carrier protein or other immunogenic protein can be used. For example, the hapten can be coupled to a T cell epitope of a bacterial toxin. See U.S. Pat. No. 5,785,973 and U.S. Pat. No. 5,601,831, the teachings of which are incorporated herein. In addition, immunogenicity of rDGP5p could be increased by conjugation of a carrier molecule, for example, dipalmityl lysine. (See Hopp, Mol. Immunol., 21:13-16 (1984)).

The peptides or proteins of this invention in monomeric or multimeric form can be incorporated into vaccines capable of inducing protective immunity against oocysts/sporozoites of T. gondii. The peptides or proteins of this invention can be administered as multivalent subunit vaccines in combination with other antigens of T. gondii. For example, they may be administered in conjunction with other oocyst/sporozoite components of T. gondii. Furthermore, it will be understood that peptides specific for a plurality of T. gondii stages and *Toxoplasma* species may be incorporated in the same vaccine composition to provide a multivalent vaccine. In addition, the vaccine composition may comprise antigens to provide immunity against other diseases in addition to toxoplasmosis.

The conjugates can be formed by standard techniques for coupling proteinaceous materials. Fusions can be expressed from fused gene constructs prepared by recombinant DNA techniques as described. Also provided herein is a fusion protein that comprises the polypeptide of the invention in all its different antigenic forms and a second unrelated polypeptide encoded by, e.g., a DNA segment operably coupled to the DNA segment encoding the polypeptide of the invention. An example of the second unrelated polypeptide is beta-galactosidase, where the DNA segment encoding this gene product also contains regulatory sequences. However, other polypeptides may also be used, such as to provide a large protein component to increase immunogenicity. If the gene encoding the polypeptide of the invention is cloned within the beta-galactosidase gene, the two polypeptides may be expressed as a fusion protein and the amount of fusion protein produced is controlled by the regulatory sequences of the beta-galactosidase gene.

Also provided herein is a biologically pure DNA segment encoding the polypeptide of the invention. In addition, provided herein are the DNA sequences for both strands of each clone. Moreover, given the degeneracy of the genetic code, there may be multiple DNA sequences encoding the same polypeptide. All are part of this invention.

The immunotherapy of toxoplasmosis in humans and animals may be conducted by the oral (intraluminal gastrointestinal) administration of the antibodies of the invention to patients with toxoplasmosis to effectively reduce their symptomatology.

Also an important part of this invention is a method of diagnosing *Toxoplasma* oocyst infection, that comprises contacting a body substance with an anti-*Toxoplasma* oocyst antibody having specificity for the polypeptide of this invention; and detecting any selective binding of the antibody to any antigenic *Toxoplasma* oocyst peptides present in the body substance. The anti-*Toxoplasma* oocyst antibodies may be monoclonal or polyclonal. Also provided herein is a method of detecting the presence of *Toxoplasma gondii* in water samples. The detection of the antibody-polypeptide complex may be conducted by any method known in the art. This includes solid phase, double antibody, sandwich double antibody, and triple antibody assays, and the like, including radioimmunoassay, enzyme-linked immunosorbent assay, fluorescent assay, including flow cytometry, chemiluminescent assay, competitive immunoassay, membrane-based immunoassay, immunomagnetic separation, precipitation, agglutination, antigen capture, or the like.

For example, flow cytometric analysis can be used to detect *T. gondii* in stool samples and in water samples. Flow cytometry is relatively rapid and easily incorporated into routine clinical hospital laboratories equipped with a flow cytometer to screen samples. Such a procedure has been described by Arrowood et al., J. Parasitol., 81(3):404-409 (1995). Briefly, fecal samples are collected from cats, diluted in 2.5% potassium dichromate, and homogenized by vortexing. Aliquots (200 μl) of the vortexed samples are centrifuged over microscale discontinuous sucrose gradients. The fractions are collected, washed, and incubated with a FITC-labeled *T. gondii*-specific mAb for 30 min at 37° C. For positive controls: fecal samples are collected from control (uninfected) cats, suspended in 2.5% potassium dichromate, and homogenized by vortexing. Purified oocysts are added to these (previously uninfected) samples at concentrations of 105, 104, 103, and 102 per ml. These control samples are centrifuged over microscale discontinuous sucrose gradients, washed, and stained as above. Volumes of samples and controls are adjusted to 600 μl with phosphate-buffered saline (PBS) and are assayed by using logical. gating of forward/side scatter and fluorescence signal on a flow cytometer. Positive control seeded samples have shown a linear correlation with the number of oocysts recovered from the gradients (Arrowood et al., 1995, supra). Flow cytometric analysis of stool samples from infected cats would be expected to be at least 10 times more sensitive than conventional immunofluorescent assays. The preceding example is set forth to illustrate the general methodology and is not intended to limit the scope of the invention. Thus, the procedure can encompass different quantities, reagents, and steps. Flow cytometric methodology is well known to one of skill in the art.

Water samples can be tested for the presence of even very low numbers of *T. gondii*, by combining magnetic separation methods, e.g., MACS, with flow cytometric methods to enrich or concentrate the low numbers of *T. gondii* in the sample. For example, *T. gondii* can be concentrated using biotin-labeled anti-*Toxoplasma*-specific mAbs, together with anti-biotin-labeled magnetic beads. Because of the microscopic size of the MAC beads, any oocysts positively selected by this method can then be stained with FITC-anti-DGP5 mAb, specific for *T. gondii*, and rapidly and specifically identified by flow cytometric analysis.

In a most preferred embodiment of the presently claimed diagnostic methods for identifying presence of *T. gondii* oocysts, the method comprises the steps of: collecting a water sample; isolating an oocyst rich fraction from the water sample by concentration with immunomagnetic methodology; staining the concentrated oocysts with *T. gondii*-specific mAb, and determining the actual number, if any, of *T. gondii* oocysts.

Additionally provided herein is a method of diagnosing *Toxoplasma* oocyst infection, that comprises contacting a body substance with one of the polypeptides of this invention; and detecting any selective binding of the polypeptide to any anti-*Toxoplasma* oocyst antibodies in the body substance. As in the previous case, the present antibody-polypeptide binding complex may be detected by a variety of methods such as those listed above. Examples of body substances are stools and other liquid or solid body output or tissue samples obtained from a subject. Examples of body fluids are blood, serum, saliva, urine, and the like. Methods for the preparation of the body substance and the body fluid are standard in the art and need not be further detailed herein (see, for example, Manual of Clinical Microbiology, Chapter 8, "Collection, Handling and Processing of Specimens", 4th edition, Eds, Lennette, E. H., et al., American Society for Microbiology (1986)).

Still part of this invention is a kit for the diagnosis of Toxoplasma oocyst infection, that comprises the peptide(s) of this invention; and instructions for use of the kit. This kit may be utilized for the detection of endogenous antibodies produced by a subject that is afflicted with toxoplasmosis. Even at the early stages where the parasite is commencing invasion of a subject's cells, some amount of *Toxoplasma* specific antibody may be detected in serum. Also provided herein is another *Toxoplasma* oocyst diagnostic kit, that comprises anti-*Toxoplasma* oocyst antibodies having specificity for one of the polypeptides of this invention; and instructions for use of the kit. Thus, kit may be utilized for the detection of *Toxoplasma* oocyst peptides, a sign that there is parasite present in the subject being tested.

In addition to the above, the kits may also comprise a control, anti-antibodies, protein A/G, and the like, suitable for conducting the different assays referred to above.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

*Toxoplasma gondii* RNA, DNA, and protein were extracted from unsporulated and sporulated oocysts, excysted sporozoites, tachyzoites, and bradyzoites stages using TRIZOL reagent (Gibco/BRL Life Technologies, Gaithersburg, Md.). For collection of parasite nucleic acids and proteins from unsporulated and sproulated oocysts, oocysyt walls were first disrupted by treating intact oocysts with 5.25% sodium hypochlorite in water for 30 minutes at room temperature. Oocysts were washed 3-4 times by centrifugation in water to remove the sodium hypochlorite, and were then disrupted by vortexing with 500 micron glass beads for 5 minutes. For collection of parasite nucleic acids and proteins from excysted sporozoites, tachyzoites, and bradyzoites, parasites were pelleted by centrifugation and lysed in 1-2 mls of TRIZOL reagent by repetitive pipetting (Hill, D. E., et al., "Specific detection of *Neospora caninum* oocysts in fecal samples from experimentally infected dogs using the polymerase chain reaction", Journal of Parasitology, 87:395-8 (2001)).

The samples were centrifuged at 12,000 ×g for 10 minutes at 4° C., and the supernatant containing RNA was collected and transferred to a fresh tube. The samples were incubated for 5 minutes at 30° C. to dissociate nucleoprotein complexes. Chloroform (0.2 ml/1 ml of TRIZOL) was then added to each sample and the tubes were shaken vigorously for 15 seconds and incubated again at 30° C. for 2 minutes, followed by centrifugation at 12,000 ×g for 15 minutes at 40° C. The aqueous phase containing the RNA was collected and transferred to a fresh tube (the organic phase containing DNA and protein was also collected). The RNA was precipitated using 0.5 ml of isopropyl alcohol per 1 ml of TRIZOL used for the initial homogenization. Samples were incubated at 30° C. for 10 minutes and centrifuged at 12,000 ×g for 10 minutes at 4° C. The supernatant was removed and the RNA pellet was washed with 2 mls of 75% ethanol. The sample was mixed by vortexing and centrifuged at 7,500 ×g for 5 minutes at 4° C. The pellet was air dried for 10 minutes then dissolved in RNase-free water and frozen until used.

Using the extracted RNA, cDNA libraries were constructed from unsporulated oocysts, sporulated oocysts, excysted sporozoites, tachyzoites, and bradyzoite life cycle stage of *T. gondii* using the Smart cDNA synthesis by long distance PCR protocol in the λTriplEx vector (Clontech, Mountain View, Calif.). First strand cDNA synthesis was accomplished using 1.0 mg total RNA, 1 ml SMART IV oligonucleotide (5'-AAGCAGTGGTATCAACGCAGAGT-GGCCATTACGGCCGGG-3')(SEQ ID NO:3), 1 ml CDS III/3' PCR primer (5'-ATTCTAGAGGCCGAGGCGGCCGA-CATG-d(T)30N-1N-3'; (N=A, G, C, or T; N-1=A, G, or C)) (SEQ ID NO:4), incubating at 72° C. for 2 minutes, and cooling the sample on ice for 2 min. Next, 2.0 ml. 5× first-strand buffer, 1.0 ml DTT (20 mM), 1.0 ml dNTP mix (10 mM), and 1.0 ml PowerScript reverse transcriptase were added, and incubating the sample at 42° C. for 1 hr. First strand synthesis was terminated by incubating the samples on ice. For second strand cDNA synthesis, 2 μl of the first strand cDNA was combined with 80 μl deionized $H_2O$, 10 μl 10× Advantage 2 PCR buffer, 2 μl 50× dNTP Mix, 2 μl 5' PCR primer (5'-AAGCAGTGGTATCAACGCAGAGT-3') (SEQ ID NO:5), 2 μl CDS III/3' PCR primer (sequence given above), and 2 μl 50× Advantage 2 polymerase mix. Samples were placed in a preheated (95° C.) Gene Amp 9600 thermal cycler, and amplification was accomplished using the following conditions: 95° C. 20 sec, then 95° C. 5 sec, 68° C. 6 min for 20 cycles. Double stranded DNA amplicons were treated with Proteinase K (20 μg/μl) to inactivate DNA polymerase activity, extracted with phenol:chloroform:isoamyl alcohol, precipitated with sodium acetate and ethanol, and centrifuged to pellet, and resuspended in $dH_2O$. The cDNA was digested with Sfi I restriction enzyme for 2 hr at 50° C. The digested cDNAs were fractionated using a CHROMA-Spin-400 column to select larger (>200 kb) cDNAs.

The Sfi I-digested and fractionated cDNA was directionally ligated into the Sfi I-digested, dephosphorylated λTriplEx2 vector and packaged using Gigapack III Gold packaging extracts (Stratagene); titering reveealed at least $1 \times 10^6$ independent clones in each unamplified library. Plasmids containing cDNA inserts were recovered from the recombinant λTriplEx phage using XL1Blue cells, and the libraries were amplified using XL1 Blue cells to titers ranging from $10^9$-$10^{10}$ pfu/ml, and stored at 4° C. until used.

Proteins were precipitated from the interphase and phenol phase of the initial TRIZOL homogenate described above with 1.5 ml of isopropyl alcohol per ml of the initial volume of TRIZOL used. Samples were incubated for 10 minutes at 30° C., then centrifuged at 12,000×g for 10 minutes at 4° C. The supernatant was discarded and the pellet was washed 3 times in 0.3 M guanidine hydrochloride in 95% ethanol. The pellet was vortexed in 2 ml of ethanol, incubated in ethanol for 20 minutes at 30° C., then centrifuged at 7,500×g for 5 minutes at 4° C. The pellet was vacuum dried 10 minutes and dissolved in 1% SDS, then stored at −20° C. until used.

Proteins extracted from each of the stages as described above were resolved. in 2-dimensional Western blots screened with swine sera from known oocyst induced infection to identify an oocyst-specific protein from *T. gondii*. Immobilized pH gradient gel strips (11 cm, pH 3-10 gradient) were rehydrated in buffer (8M urea, 2% CHAPS, 2 mM TBP, 0.2% Bio-Lytes 3/10, and 0.001% bromophenol blue) containing 125 μg of *T. gondii* solubilized proteins from the extraction procedure described above at 50V for 12 hrs, followed by focusing at 5000V for 35,000 Vh using the BioRad IPG focusing cell. Strips containing focused proteins were soaked at room temperature in equilibration buffer (6M urea, 0.375 M Tris-HCl, pH 8.8, 2% SDS, 20% glycerol, 2% dithiothreitol) for 30 min and electrophoresed in the $2^{nd}$ dimension on 4-12% gradient Bis-Tris gels (Invitrogen, Carlsbad, Calif.) in 50 mM MOPS-SDS running buffer (50 mM 3-N-morpholino propane sulfonic acid, 50 mM Tris base, 3.5 mM SDS, 1 mM EDTA, pH 7.7) at 150V for 75 min. All 2-D gel supplies, including 2-D analysis software, unless otherwise noted, were purchased from BioRad Laboratories (Hercules, Calif.). Electroblotting was carried out on unfixed gels by transfer of proteins onto Immobilon (PVDF) nylon blotting membrane (Millipore, Bedford, Mass.) using a Novex gel transfer apparatus (Novex, San Diego, Calif.) set at 40V for 80 min in 25 mM Bicine, 25 mM Bis-Tris, 1 mM EDTA, 20% methanol, pH 7.2 blotting buffer. For Western blotting, the membranes were rinsed in 50 mM Tris buffered, 0.85% saline (TBS) and unbound sites on the membrane were saturated with Detector Block solution (Kirkegaard and Perry, Gaithersburg, Md.). The membrane was incubated in a pool of porcine sera (diluted 1:500) from 10 pigs with acute oocyst-induced *T. gondii* infection (~1000 oocyst per os; positive MAT titer of ≧1:400; pool prepared from sera taken from week 4 through week 12 post infection). Horseradish peroxidase conjugated-goat anti-pig IgG (Sigma Chemical. St. Louis, Mo.) was used as the $2^{nd}$ step antibody at a dilution of 1:800. Oocyst proteins recognized by porcine anti-*Toxoplasma* antibodies were visualized using the 4CN membrane developer kit (Kirkegaard and Perry, Gaithersburg, Md.). Western blot images were captured using the ProExpress proteomics image acquisition system (Perkin Elmer, Boston, Mass.); spot matching and image analysis of the 2-D Western blot images was accomplished using the PDQuest software system. Identical 2-D gels containing oocyst proteins were stained with Sypro Ruby stain (BioRad, Hercules, Calif.), and the 2-D images were analyzed for spot matching and comparisons to the Western blot images using the PD Quest software. Matching spots were excised from the Sypro Ruby stained gels and analyzed by matrix assisted laser desorption/ionization-time of flight mass spectrometry (MALDI-TOF-MS) and collision induced dissociation (CID) fragmentation. FIG. 1 shows the Matrix assisted laser desorption/ionization time of flight spectra (MALDI-TOF) of peptide masses resulting from digestion of DGP5p+ excised 2-dimensional gel spot; the peptide mass "fingerprint" gives the identity of the protein and is unique to a protein, and when fed into the mass fingerprint database (Mascot) it gives the specific identity of the protein (shown in the table-below). The following table indicates the protein characteristics (size, isoelectric point) of the DGP5p+ protein predicted by the MALDI spectral data (MOWSE (Molecular Weight SEarch) score indicates the likelihood that the identification is a random event, a score over 70 indicates a good match; the score below was over 1000, with mass data on 45% of the peptides):

Tubes were incubated 16° C. overnight, then packaged into the λ-phage vector and titered; and sequenced on an ABI Sequencer model 3100.

The sequenced PCR amplicon was as follows: (ATGGCGTCTGTAAAACGCGTCGTTGTGGCGGTAATGATCGTGAACGTGCTGGCTTTAATTTTTGTGGGCGTTGCCGGTTCAACGCGTGACGTAGGGTCAGGCGCGGATGACTCCGAAGGTGCTGGAGGGCGTGAACGACAACAGGTACAACAACACGAACAAAATGAAGACCGATCGTTATTCGAAAGGGGAAGAGCAGCGGTGACTGGACATCCAGTGAGGACTGCAGTGGGACTTGCTGCAGCTGTGGTGGCCGTTGTGTCACTACTGCGATTGTTGAAAAGGAGGAGAAGACGCGCGATTCAAGAAGAGAGCAAGGAGTCTGCAACCGCGGAAGAGGAAGAAGTTGCCGAGGAAGAGTAAG) (SEQ ID No. 8) for the sporozoite DGP, identified above as a potential gene candidate for further study for developing an assay to identify route of infection with *T. gondii*, were labeled using a non-radioactive digoxigenin (DIG) DNA labeling kit.(Roche Applied Sciences) for use in library screening to isolate the full length gene for protein expression.

DIG-labeled DNA probes were generated by denaturing 10 ng of the above PCR amplicon DNA at 100° C. for 10 minutes, chilling on ice, then adding a hexanucleotide mix (2 ul), dNTP labeling mix (2 ul) and Klenow fragment enzyme (1 ul). The mixture was incubated for 8 hours at 37° C., and the reaction was stopped using 2ul 0.2M EDTA (pH 8.0). The sporozoite cDNA library was screened using the DIG labeled PCR amplicons as probes. The sporozoite cDNA library, plated onto LB-Ampicillin plates overnight at 37° C., was transferred to nitrocellulose filters. Filters were placed sequentially on filter paper soaked with 0.5M NaOH, 1M Tris-Cl, and 0.5MTris Cl/1.25M NaCl, then dried at 80° C. in a vacuum oven. Filters were probed with the digoxigenin labeled DNA probes described above in SSC hybridization buffer at 45° C., and positive clones were detected after fixation and hybridization by an anti-digoxigenin antibody conjugated to the enzyme alkaline phosphatase which catalyzes a colorometric reaction with the substrate horseradish peroxidase. Approximately 20 positive clones were identified and

| MOWSE Score | % Cov | Mean Err ppm | Data Tol ppm | Protein MW (Da)/pI | Species | Protein Name |
|---|---|---|---|---|---|---|
| 1.03E+04 | 45 | −28.1 | 105 | 12977/5.8 | TOXGONDII | DENSE GRANULE PROTEIN 5 PRECURSOR (PROTEIN GRA 5)(P21) |

Searching the non-redundant database with Mascot, and the invertebrate databases from SwissProt and Trembl identified one of the highly immunoreactive proteins as a sporozoite dense granule protein.

Polymerase chain reaction (PCR) primers were constructed from the amino acid sequence (forward: GAA TTC ATG GCG TCT GTA AAA CGC (SEQ ID NO:6); (reverse: AAG CTT CTT ACT CTT CCT CGG CAA CT (SEQ ID NO:7)) derived from the mass spectrometry and database searches, and PCR was performed using the primers listed above and DNA extracted from the sporozoite cDNA library. The amplicons produced were ligated into the pTriplEx2 plasmid vector using 1.5 μl of cDNA, 1.0 μl of vector plasmid, 0.5 μl of 10× ligation buffer, 0.5 μl ATP, 0.5 μl T4 DNA ligase, and 1.0 μl deionized water. The reagents were added to a tube, mixed gently, and briefly spun to bring contents to the bottom.

selected. Secondary screening resulted in selection of over 50 positive plaques, and 12 were sequenced to confirm the DGP5p gene (SEQ ID No. 2); part of this sequence (in bold below) was the DIG labeled amplicon (SEQ ID No. 8) used above as the probe:

```
(GGGTGGCATGACTCCCTCAGGTGGTTAGCGGAGAAACCTCAGATCCCTC

GGCGCGCGACGCGTGCCAGAGCGCGGGACGGGGTGGCAACGAGACACGTT

TGGATAAAGGTCCTGCCAGGTTGTGGAATCAGACGTGTGGGCTGTTCCGC

GTCGGTTTGGTTTGTGCAGAGACGCACTGACGGTTGACGTCGATCGGCAC

TCGATCCTACCGTCAGTCAATTTTATTTTGGTTTTTGCAGATATCATCGC
```

-continued

```
GCGTGTGTTCACTCTAACTGTGTGTATGGTTCACTGTTTTTATTGCGAT

TTTCGTGAAGTAACAAAATGGCGTCTGTAAAACGCGTCGTTGTGGCGGTA

ATGATCGTGAACGTGCTGGCTTTAATTTTTGTGGGCGTTGCCGGTTCAAC

GCGTGACGTAGGGTCAGGCGCGGATGACTCCGAAGGTGCTGGAGGGCGTG

AACGACAACAGGTACAACAACACGAACAAAATGAAGACCGATCGTTATTC

GAAAGGGGAAGAGCAGCGGTGACTGGACATCCAGTGAGGACTGCAGTGGG

ACTTGCTGCAGCTGTGGTGGCCGTTGTGTCACTACTGCGATTGTTGAAAA

GGAGGAGAAGACGCGCGATTCAAGAAGAGAGCAAGGAGTCTGCAACCGCG

GAAGAGGAAGAAGTTGCCGAGGAAGAGTAAGGGGCACTGTGTTGCTCGGC

TCTTTGTTGTCTCAGCGTGAGGATTTAGTGCGTGTAGCGCAGCATGTATC

GATCGATACAGGCACGGTTGGACGTGTCGTCTGTATCCCTTGTGGCAGAC

GGCAGACGCCATTGTCAGAGCGTGTTGCACGTTGGAAGAAAATGTGTTGG

TGTAATCCCTCGTCGGACAGATACCAGGAGGTTGCGTGGTGATGATCGTG

TGTGCGTAGAGGTGTGCCTCGTGATAACATGAAGGGCAAGGACCTTTTTT

GTCGAGCACATACTCAAACCAGTGATTGTGCGAGGCGGGTTGCACGCGAC

TTTGATCCATTACAGTTAAATATGCCGAACGCGTGGCCTGATTCGCACAC

AAGGCGCACAGACGTACCGTTGATGAG).
```

The selected clones were diluted in lambda buffer, expanded in XL1 Blue cells, and plated on LB agar at 40° C. for 5 hours. Expression of the insert was induced in XL1 Blue cells by overlaying the plates with IPTG-soaked nitrocellulose filters for 4 hours. Filters were removed, blocked with TBS-Tween and 1% gelatin, and immunologically screened using *T. gondii* oocyst-infected human sera. Positive results from the immunoscreen confirmed that the clones were reactive with the infection sera.

The identified DGP5p gene was subcloned into the EcoRI/Hind III site of pMal-c2 vector (New England Biolabs, Beverly, Ma.) for constitutive protein expression and was expressed as an N-terminal maltose binding fusion protein under the control of the lac repressor. The translated open reading frame of rDGP5p was as follows: (ORF-SNKMA-SVKRVVVAVMIVNVLALIFVGVAGSTRDVGSGADDS-EGAGGRERQQVQQHEQNEDRSLFERGRAAVTGHPV-RTAVGLAAAVVAVVSLLRLLKRRRRRAIQESKESATA-EEEEVAEEE)(SEQ ID No. 1). Expression of the fusion protein was induced with IPTG; the protein was purified using an amylose resin column which binds to the maltose binding protein. The fusion protein was eluted from the column with 10 mM maltose, and column fractions were analyzed at 280 nm to determine which fractions contained the fusion protein. The fractions of interest were pooled and concentrated using a centriprep spin column to a minimum of 1 mg/ml. The fusion protein was cleaved using Factor Xa, and purified using DEAE-Sepharose ion exchange chromatography. Western blots were carried out to assure continued serological reactivity of the expressed purified protein. The recombinant protein was initially probed with sera from pigs that were experimentally infected with *T. gondii* oocysts (sera collected week 2-6 of infection), followed by probing with human sera from oocyst induced infections.

The recombinant protein was then used to develop an ELISA assay. The following sera were used to validate the specificity and sensitivity of the assay: human serum from infections resulting from ingestion of *T. gondii* oocysts during an accidental laboratory exposure; sera from a CDC-documented oocyst induced outbreak which occurred near Atlanta, Georgia; serum collected during an outbreak in a religious community in Illinois which was known to have resulted from oocyst exposure; and serum from congenitally infected children. For the ELISA, optimal dilution of the purified recombinant antigen was initially determined using 2 fold dilutions beginning at 10 µg/mL down to 0.1 µg/mL and tested in the ELISA format using a positive control human serum, (diluted 1:500), whose anti-*Toxoplasma* IgM EIA value exceeded 6.0 as determined by a commercial laboratory. One hundred microliters (100 µL) of the optimal dilution of the recombinant antigen of 1 µg/mL in 0.1M carbonate buffer, pH 9.6, was used to coat each well of a high binding, flat bottomed microtitre plate (Costar). The plates were incubated overnight at 4° C., and were then washed with 0.5M phosphate buffered saline containing 0.5% Tween 20 (PBS-T) and incubated with human serum samples diluted 1:500 overnight at room temperature. Anti-human IgM or IgG peroxidase conjugated antibody, diluted 1:1000, was used as the second step antibody and was added to the wells and incubated for 4 hours at room temperature. After washing the plates, ABTS peroxidase microwell substrate (KPL) was added to each well and incubated for 5 minutes. Plates were read at 405 nm using a Vmax ELISA reader (Molecular Devices). Positive and negative control sera were included on each plate. A positive cut-off was established as 5 times the mean ± standard deviation of the mean of a set of 14 *Toxoplasma* negative human serum samples. Positive and negative predictive values were calculated. All serum samples were also analyzed using anti-*Toxoplasma* MAT as the gold standard for comparative purposes.

Figure 2:
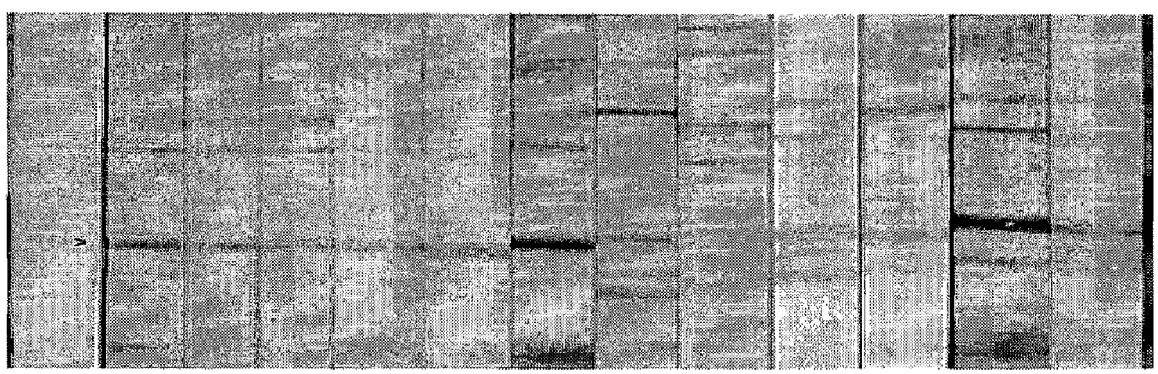
FIG. 2 shows the immunostaining of Western blot cleaved (unpurified) fusion protein: Lanes 1-13, strips incubated in swine antibody from oocyst induced infection with *T. gondii*; lane 1 & 2 sera from same pig, lanes 3-13 10 individual swine sera from oocyst infected pigs. Lane 1 antigen, uninduced fusion protein. Lane 2 -13 antigen, induced fusion protein.

Results: To test the recombinant antigen, the Factor Xa-cleaved antigen preparation was initially tested in Western blots (before purification using DEAE sepharose chromatography) using sera from pigs infected with *Toxoplasma* oocysts; the results of these tests are shown in FIG. 2. Lane 1 contains the Factor Xa-cleaved pMal-c2 vector without the DGP5p insert. Lanes 2-13 contain the factor cleaved pMal-c2 vector with the DGP5p insert probed with individual sera from pigs experimentally infected with *T. gondii* oocysts. Results indicated reactivity of recombinant protein with pig sera derived from animals infected with *T. gondii* oocysts.

Figure 3:
FIG. 3 shows the immunostaining of Western blot purified recombinant protein (described below): Lane 1, human antibody from congenital infection with *T. gondii*. Lanes 2-7, human antibody from oocyst induced infection with *T. gondii*.

Human sera were also tested in Western blots with the recombinant antigen after passage of the Factor Xa cleaved-preparation over a DEAE sepharose- column for purification. Lane 1 contains the Factor Xa-cleaved, DEAE column purified pMal-c2 vector without the DGP5p insert. Lanes 2-7 contain the Factor Xa-cleaved, DEAE column purified pMal-c2 vector with the DGP5p insert, probed with individual sera from humans with *T. gondii* oocyst-induced infections. These results demonstrated continued serological reactivity of human serum to the purified recombinant protein after isolation (FIG. 3).

Sera from 40 oocyst infected pigs and 45 tissue cyst infected pigs was tested in ELISA and MAT following confirmation of infection by bioassay (Table 1):

TABLE 1

MAT titers and ELISA results for pig sera.

| Swine sera sources | MAT (titer) | | | | | ELISA (IgG) | |
| --- | --- | --- | --- | --- | --- | --- | --- |
| | 0 | 1:10 | 1:25 | 1:100 | 1:500 | Positive | Negative |
| Swine sera from oocyst induced infection | 0 | 0 | 0 | 2 | 38 | 39 | 1 |
| Swine sera from tissue cyst induced infection | 0 | 0 | 0 | 6 | 39 | 3 | 42 |

Of the 40 pigs infected with oocysts, surprisingly 39 of were correctly detected using the recombinant antigen ELISA. Forty-five pigs were infected via consumption of tissue cysts, surprisingly only 3 of these animals were positive by the recombinant antigen ELISA.

ELISA and MAT assays were also completed on 127 human sera known to have resulted from oocyst exposure, 5 sera from infections resulting from congenital infection, and 76 sera from MAT negative individuals (Tables 2 and 3):

TABLE 2

MAT titers and ELISA results for human sera.

| Human sera sources | MAT (titer) | | | | | ELISA (IgG) | |
| --- | --- | --- | --- | --- | --- | --- | --- |
| | 0 | 1:10 | 1:25 | 1:100 | 1:500 | Positive | Negative |
| Accidental lab exposure to oocysts (n = 7) | 0 | 0 | 0 | 0 | 7 | 7 | 0 |
| Atlanta outbreak (n = 17) | 0 | 0 | 0 | 2 | 15 | 15 | 2 |
| Illinois outbreak (n = 20) | 0 | 0 | 0 | 1 | 19 | 19 | 1 |
| Congenital infection (n = 5) | 0 | 0 | 0 | 2 | 3 | 0 | 5 |
| Waterborne outbreak (n = 83) | 0 | 5 | 8 | 27 | 43 | 78 | 5 |
| Negative control serum (n = 76) | 75 | 1 | 0 | 0 | 0 | 0 | 76 |

TABLE 3

Positive (PPV) and negative predictive values (NPV) for the MAT and ELISA using human sera based on sensitivity.

| Samples | | MAT | ELISA (IgG) |
| --- | --- | --- | --- |
| Oocyst induced infection | PPV | 100 | 93.7 |
| Negative control sera and tissue cyst induced infection | NPV | 98.6 | 100 |

The results shown in Tables 2 and 3 surprisingly demonstrated comparable sensitivity of the 2 assays and specific detection of antibody in sera from oocyst induced infections using the recombinant antigen. Results from ELISAs using anti-human IgG are shown; recombinant antigen-specific IgM responses were not sufficiently robust and did not persist for more than 4 months in greater that 80% of samples analyzed. Of 76 uninfected sera (as confirmed by MAT) all were negative using the recombinant ELISA. Of 127 oocyst induced infections, the recombinant antigen ELISA surprisingly detected 119, and did not detect 8, resulting in a PPV of 93.7% as compared to the MAT of 100%. Infections induced by congenital transmission were not detected using the recombinant antigen ELISA.

The following table indicated that 3 linear B-cell epitopes in rDGP5p (amino acids 29-62, 69-77, and 103-123) were likely to stimulate antibody production:

```
BedipiPred 1.0b Server - prediction results
source-version bepipred-1.0b
Type: Protein Sequence
Protein Sequence:
SNKMASVKRVVVAVMIVNVLALIFVGVAGSTRDVGSGADDSEGAGGRERQQVQQHEQ
NEDRSLFERGRAAVTGHPVRTAVGLAAAVVAVVSLLRLLKRRRRRAIQEESKESATAEE
EEVAEEE end-Protein (SEQ ID No. 1
seqname # source     feature      start   end     score N/A?

Sequence   bepipred-1.0b epitope    1       1       0.387 .. E

Sequence   bepipred-1.0b epitope    2       2       0.415 .. E

Sequence   bepipred-1.0b epitope    3       3       0.222 .. .
```

-continued

| Sequence | bepipred-1.0b epitope | 4 | 4 | 0.236 | . | . |
|---|---|---|---|---|---|---|
| Sequence | bepipred-1.0b epitope | 5 | 5 | 0.160 | . | . |
| Sequence | bepipred-1.0b epitope | 6 | 6 | -0.210 | . | . |
| Sequence | bepipred-1.0b epitope | 7 | 7 | -0.532 | . | . |
| Sequence | bepipred-1.0b epitope | 8 | 8 | -0.856 | . | . |
| Sequence | bepipred-1.0b epitope | 9 | 9 | -0.897 | . | . |
| Sequence | bepipred-1.0b epitope | 10 | 10 | -1.106 | . | . |
| Sequence | bepipred-1.0b epitope | 11 | 11 | -1.439 | . | . |
| Sequence | bepipred-1.0b epitope | 12 | 12 | -1.679 | . | . |
| Sequence | bepipred-1.0b epitope | 13 | 13 | -1.972 | . | . |
| Sequence | bepipred-1.0b epitope | 14 | 14 | -1.965 | . | . |
| Sequence | bepipred-1.0b epitope | 15 | 15 | -1.952 | . | . |
| Sequence | bepipred-1.0b epitope | 16 | 16 | -2.091 | . | . |
| Sequence | bepipred-1.0b epitope | 17 | 17 | -2.054 | . | . |
| Sequence | bepipred-1.0b epitope | 18 | 18 | -2.332 | . | . |
| Sequence | bepipred-1.0b epitope | 19 | 19 | -2.446 | . | . |
| Sequence | bepipred-1.0b epitope | 20 | 20 | -2.547 | . | . |
| Sequence | bepipred-1.0b epitope | 21 | 21 | -2.435 | . | . |
| Sequence | bepipred-1.0b epitope | 22 | 22 | -2.148 | . | . |
| Sequence | bepipred-1.0b epitope | 23 | 23 | -2.181 | . | . |
| Sequence | bepipred-1.0b epitope | 24 | 24 | -1.897 | . | . |
| Sequence | bepipred-1.0b epitope | 25 | 25 | -1.398 | . | . |
| Sequence | bepipred-1.0b epitope | 26 | 26 | -1.013 | . | . |
| Sequence | bepipred-1.0b epitope | 27 | 27 | -0.391 | . | . |
| Sequence | bepipred-1.0b epitope | 28 | 28 | 0.072 | . | . |
| Sequence | bepipred-1.0b epitope | 29 | 29 | 0.664 | . | E |
| Sequence | bepipred-1.0b epitope | 30 | 30 | 0.846 | . | E |
| Sequence | bepipred-1.0b epitope | 31 | 31 | 1.007 | . | E |
| Sequence | bepipred-1.0b epitope | 32 | 32 | 1.277 | . | E |
| Sequence | bepipred-1.0b epitope | 33 | 33 | 1.448 | . | E |
| Sequence | bepipred-1.0b epitope | 34 | 34 | 1.440 | . | E |
| Sequence | bepipred-1.0b epitope | 35 | 35 | 1.580 | . | E |
| Sequence | bepipred-1.0b epitope | 36 | 36 | 1.690 | . | E |
| Sequence | bepipred-1.0b epitope | 37 | 37 | 1.859 | . | E |
| Sequence | bepipred-1.0b epitope | 38 | 38 | 1.908 | . | E |
| Sequence | bepipred-1.0b epitope | 39 | 39 | 2.187 | . | E |
| Sequence | bepipred-1.0b epitope | 40 | 40 | 2.152 | . | E |
| Sequence | bepipred-1.0b epitope | 41 | 41 | 2.185 | . | E |
| Sequence | bepipred-1.0b epitope | 42 | 42 | 2.142 | . | E |
| Sequence | bepipred-1.0b epitope | 43 | 43 | 2.156 | . | E |

-continued

| Sequence | bepipred-1.0b epitope | 44 | 44 | 2.031 | .. E |
|---|---|---|---|---|---|
| Sequence | bepipred-1.0b epitope | 45 | 45 | 1.824 | .. E |
| Sequence | bepipred-1.0b epitope | 46 | 46 | 1.678 | .. E |
| Sequence | bepipred-1.0b epitope | 47 | 47 | 1.515 | .. E |
| Sequence | bepipred-1.0b epitope | 48 | 48 | 1.221 | .. E |
| Sequence | bepipred-1.0b epitope | 49 | 49 | 1.168 | .. E |
| Sequence | bepipred-1.0b epitope | 50 | 50 | 1.058 | .. E |
| Sequence | bepipred-1.0b epitope | 51 | 51 | 0.931 | .. E |
| Sequence | bepipred-1.0b epitope | 52 | 52 | 0.965 | .. E |
| Sequence | bepipred-1.0b epitope | 53 | 53 | 0.929 | .. E |
| Sequence | bepipred-1.0b epitope | 54 | 54 | 1.073 | .. E |
| Sequence | bepipred-1.0b epitope | 55 | 55 | 1.183 | .. E |
| Sequence | bepipred-1.0b epitope | 56 | 56 | 1.345 | .. E |
| Sequence | bepipred-1.0b epitope | 57 | 57 | 1.483 | .. E |
| Sequence | bepipred-1.0b epitope | 58 | 58 | 1.425 | .. E |
| Sequence | bepipred-1.0b epitope | 59 | 59 | 1.018 | .. E |
| Sequence | bepipred-1.0b epitope | 60 | 60 | 0.646 | .. E |
| Sequence | bepipred-1.0b epitope | 61 | 61 | 0.533 | .. E |
| Sequence | bepipred-1.0b epitope | 62 | 62 | 0.421 | .. E |
| Sequence | bepipred-1.0b epitope | 63 | 63 | 0.332 | .. . |
| Sequence | bepipred-1.0b epitope | 64 | 64 | 0.224 | .. . |
| Sequence | bepipred-1.0b epitope | 65 | 65 | -0.020 | .. . |
| Sequence | bepipred-1.0b epitope | 66 | 66 | -0.097 | .. . |
| Sequence | bepipred-1.0b epitope | 67 | 67 | -0.201 | .. . |
| Sequence | bepipred-1.0b epitope | 68 | 68 | 0.195 | .. . |
| Sequence | bepipred-1.0b epitope | 69 | 69 | 0.693 | .. E |
| Sequence | bepipred-1.0b epitope | 70 | 70 | 0.740 | .. E |
| Sequence | bepipred-1.0b epitope | 71 | 71 | 0.785 | .. E |
| Sequence | bepipred-1.0b epitope | 72 | 72 | 0.594 | .. E |
| Sequence | bepipred-1.0b epitope | 73 | 73 | 0.638 | .. E |
| Sequence | bepipred-1.0b epitope | 74 | 74 | 0.648 | .. E |
| Sequence | bepipred-1.0b epitope | 75 | 75 | 0.672 | .. E |
| Sequence | bepipred-1.0b epitope | 76 | 76 | 0.604 | .. E |
| Sequence | bepipred-1.0b epitope | 77 | 77 | 0.567 | .. E |
| Sequence | bepipred-1.0b epitope | 78 | 78 | 0.112 | .. . |
| Sequence | bepipred-1.0b epitope | 79 | 79 | 0.007 | .. . |
| Sequence | bepipred-1.0b epitope | 80 | 80 | -0.156 | .. . |
| Sequence | bepipred-1.0b epitope | 81 | 81 | -0.162 | .. . |
| Sequence | bepipred-1.0b epitope | 82 | 82 | -0.457 | .. . |
| Sequence | bepipred-1.0b epitope | 83 | 83 | -0.674 | .. . |

-continued

| | | | | | |
|---|---|---|---|---|---|
| Sequence | bepipred-1.0b epitope | 84 | 84 | -0.826 | . . |
| Sequence | bepipred-1.0b epitope | 85 | 85 | -0.874 | . . |
| Sequence | bepipred-1.0b epitope | 86 | 86 | -1.139 | . . |
| Sequence | bepipred-1.0b epitope | 87 | 87 | -0.953 | . . |
| Sequence | bepipred-1.0b epitope | 88 | 88 | -1.338 | . . |
| Sequence | bepipred-1.0b epitope | 89 | 89 | -1.666 | . . |
| Sequence | bepipred-1.0b epitope | 90 | 90 | -1.808 | . . |
| Sequence | bepipred-1.0b epitope | 91 | 91 | -2.068 | . . |
| Sequence | bepipred-1.0b epitope | 92 | 92 | -2.233 | . . |
| Sequence | bepipred-1.0b epitope | 93 | 93 | -2.137 | . . |
| Sequence | bepipred-1.0b epitope | 94 | 94 | -1.981 | . . |
| Sequence | bepipred-1.0b epitope | 95 | 95 | -1.753 | . . |
| Sequence | bepipred-1.0b epitope | 96 | 96 | -1.681 | . . |
| Sequence | bepipred-1.0b epitope | 97 | 97 | -1.281 | . . |
| Sequence | bepipred-1.0b epitope | 98 | 98 | -0.898 | . . |
| Sequence | bepipred-1.0b epitope | 99 | 99 | -0.759 | . . |
| Sequence | bepipred-1.0b epitope | 100 | 100 | -0.552 | . . |
| Sequence | bepipred-1.0b epitope | 101 | 101 | -0.071 | . . |
| Sequence | bepipred-1.0b epitope | 102 | 102 | 0.147 | . . |
| Sequence | bepipred-1.0b epitope | 103 | 103 | 0.399 | . E |
| Sequence | bepipred-1.0b epitope | 104 | 104 | 0.583 | . E |
| Sequence | bepipred-1.0b epitope | 105 | 105 | 0.760 | . E |
| Sequence | bepipred-1.0b epitope | 106 | 106 | 0.943 | . E |
| Sequence | bepipred-1.0b epitope | 107 | 107 | 1.139 | . E |
| Sequence | bepipred-1.0b epitope | 108 | 108 | 1.267 | . E |
| Sequence | bepipred-1.0b epitope | 109 | 109 | 1.630 | . E |
| Sequence | bepipred-1.0b epitope | 110 | 110 | 1.592 | . E |
| Sequence | bepipred-1.0b epitope | 111 | 111 | 1.657 | . E |
| Sequence | bepipred-1.0b epitope | 112 | 112 | 1.675 | . E |
| Sequence | bepipred-1.0b epitope | 113 | 113 | 1.662 | . E |
| Sequence | bepipred-1.0b epitope | 114 | 114 | 1.657 | . E |
| Sequence | bepipred-1.0b epitope | 115 | 115 | 1.389 | . E |
| Sequence | bepipred-1.0b epitope | 116 | 116 | 1.250 | . E |
| Sequence | bepipred-1.0b epitope | 117 | 117 | 1.360 | . E |
| Sequence | bepipred-1.0b epitope | 118 | 118 | 1.412 | . E |
| Sequence | bepipred-1.0b epitope | 119 | 119 | 1.527 | . E |
| Sequence | bepipred-1.0b epitope | 120 | 120 | 1.441 | . E |
| Sequence | bepipred-1.0b epitope | 121 | 121 | 1.322 | . E |

| -continued | | | | | |
|---|---|---|---|---|---|
| Sequence | bepipred-1.0b epitope | 122 | 122 | 1.239 | .. E |
| Sequence | bepipred-1.0b epitope | 123 | 123 | 1.151 | .. E |

Discussion: Analysis of serum from experimentally infected pigs demonstrated that specific IgG was detectable 2 weeks post infection and persisted for 4-6 months in pigs infected with oocysts. Swine IgM generated against the recombinant antigen was weakly detectable 2 weeks post infection, but was not detectable 10 weeks post infection. For many of the recombinant antigen positive human serum samples, the actual infection date was not known so that no definitive conclusion could be drawn concerning how long the recombinant specific IgG persisted in the human host. However, 24 of the recombinant antigen positive human serum samples were drawn from people whose infection date could be closely estimated. In these samples, antigen specific IgG could be detected for at least 6 months post infection. IgG antibody reacting with the recombinant antigen was detectable within 2 weeks of infection in all positive samples tested for which the infection date is known; IgM antibody was also detectable within 2 weeks, however, the specific IgG antibody persisted at higher titer for at least 6 months while the IgM titer decreased over this time period. The specificity of the antigen can only be estimated since no human sera were available from patients infected with other protozoan parasites; however, 76 MAT negative sera from human patients were also negative in the recombinant ELISA assay, demonstrating a lack of non-specific binding to the recombinant antigen. These sera were drawn from patients with gastrointestinal nematode infections and patients with inflammatory bowel disease. In addition, *T. gondii* infected human sera which reacted strongly with the isolated recombinant antigen in the Western blots revealed only limited non-specific binding to large molecular weight proteins (>50 kDa) extracted from other protozoan parasites, including the closely related *Neospora caninum, Hammondia hammondi*, and *Sarcocystis cruzi*.

Thus the ELISA assay developed was surprisingly both sensitive and specific for the detection of human antibody to *Toxoplasma gondii* infection initiated by consumption of infectious oocysts. The ELISA assay and similar immunological assays will be useful for planned large scale surveys of human serum banks to determine the predominant route of exposure of humans to *T. gondii*, and will be helpful in the development of strategies to reduce and eliminate exposure.

All of the references cited herein are incorporated by reference in their entirety. Also incorporated by reference in their entirety are the following references: Appleford, P. J., and J. E. Smith, Int. J. Parasitol., 30:1187-91 (2000); Aramini, J. J., et al., J. Parasitol., 84:438-40 (1998); Aramini, J. J., et al., Epidemiol. Infect., 122:305-15 (1999); Bahia-Oliveira, L. M. G., et al., Int. J. Parasitol., 31:133-36 (2001); Barberi, A., et al., J. Infect. Dis., 184:944-46 (2001); Chen, X. G., et al., Prot. Exp. and Purif., 23:33-7 (2001); Cook, A. J. C., et al., Br. Med. J., 321:142-47 (2000); Dando, C., et al., J. Clin. Mic., 39:2122-25 (2001); Dubey, J. P., and C. P. Beattie, Toxoplasmosis of animals and man. Boca Raton, Fla.: CRC Press, 1988; Dubey, J. P., et al., J. Exp. Med., 132:636-62 (1970); Dubey, J. P., and J. K. Frenkel, J. of Protozool., 23:537-46 (1976); Dubey, J. P., et al., J. Parasitol., 81:48-53 (1995); Dubey, J. P., et al., Int. J. Parasitol., 32:99-105 (2002); Dubey, J. P., and K. Odening, *Parasitic Diseases of Wild Mammals*, Ames: Iowa State University Press, 2001; Greiner, M., and I. A. Gardner, Preventive Veterinary Medicine, 45(1-2):3-22 (2000); Greiner, M., and I. A. Gardner, Preventive Veterinary Medicine, 45(1-2):43-59 (2000)); Isaac-Renton, J., et al., Appl. Enviro., 64:2278-80 (1998); Kasper, L. H., Infect. Immun., 57:668-72 (1989); Kasper, L. H., et al., J. Immunol., 132:443-49 (1984); Lopez, A., et al., Morbidity and Mortality Weekly Report, 49:59-75 (2000); Lunde, M. N., L. Jacobs, J. Parasitol., 69:806-8 (1983); Omata, Y.,et al., Parasitol. Res., 75:189-93 (1989); Paweletz, C. P., et al., Drug Dev. Res., 49:34-42 (2000); Petersen, E. K., ARMIS, 96:820-24 (1988); Roberts, A., et al., Eur. J. Clin. Microbiol. Infect. Dis., 20:467-74 (2001); Smith, J. L., J. Food Prot., 56:630-39 (1993); Tenter, A. M., et al., Int. J. Parasitol., 30:1217-58 (2000); Tomavo, S., et al., Infect. Immun., 59:3750-53 (1991); Weiss, L. M., and K. Kim, Front. Sci., 5:391-405 (2000); Wright, G. L., et al., Prostate Cancer and Prostatic Dis., 2:264-76 (1999). Also incorporated by reference in its entirety is U.S. Pat. No. 6,710,166.

Thus, in view of the above, the present invention concerns (in part) the following:

An isolated (or recombinant) *Toxoplasma gondii* oocyst protein comprising (or consisting essentially of or consisting of) the amino acid sequence of SEQ ID NO: 1.

A composition comprising (or consisting essentially of or consisting of) the isolated (or recombinant) protein above and a carrier.

An isolated (or recombinant) *Toxoplasma gondii* oocyst protein having the amino acid sequence given in SEQ ID NO:1 or a part thereof, wherein said part thereof binds specifically to an antibody that specifically binds to the *Toxoplasma gondii* oocyst protein comprising (or consisting essentially of or consisting of) the amino acid sequence given in SEQ ID NO:1.

A method for the differential diagnosis of *Toxoplasma gondii* infection, comprising (or consisting essentially of or consisting of): (a) contacting the above composition with a biological sample and (b) detecting the immunological complexes formed between *Toxoplasma gondii* oocyst protein of the composition and antibodies in the biological sample, wherein the presence of immunological complexes is indicative of the presence of *Toxoplasma gondii* in the biological sample. The above method, wherein said method comprises (or consists essentially of or consists of) an ELISA.

An isolated (or recombinant) DNA molecule consisting of a nucleotide sequence encoding one or more epitopes of rDGP5p protein wherein said rDGP5p protein comprises (or consists essentially of or consists of) an amino acid sequence shown in SEQ ID NO:1 and wherein said protein is antigenic and effective to elicit an immune response against *Toxoplasma gondii* oocysts in a host animal. A recombinant DNA molecule comprising (or consisting essentially of or consisting of) the above DNA molecule of inserted therein. The above DNA molecule wherein said molecule is a cDNA molecule encoding rDGP5p protein.

The above DNA molecule consisting of the nucleotide sequence of nucleotides 1 through 369 of SEQ ID No. 2. A recombinant DNA molecule comprising (or consisting essentially of or consisting of) the above DNA molecule inserted therein.

An isolated (or recombinant) DNA molecule consisting of a fragment of the nucleotide sequence encoding one or more epitopes of rDGP5p protein wherein said fragment encodes at least one epitope of rDGP5p protein and wherein said epitope of rDGP5p protein comprises (or consists essentially of or consists of) an amino acid sequence shown in SEQ ID NO:1 and is antigenic and effective to elicit an immune response against *Toxoplasma gondii* oocysts in a host animal. The above DNA molecule wherein said molecule is a cDNA molecule encoding at least one epitope of rDGP5p protein. A recombinant DNA molecule comprising (or consisting essentially of or consisting of) the above DNA molecule inserted therein.

A vector comprising (or consisting essentially of or consisting of) a regulatory DNA segment operably coupled to a DNA nucleotide sequence encoding one or more epitopes of rDGP5p protein wherein said rDGP5p protein comprises (or consists essentially of or consists of) an amino acid sequence shown in SEQ ID NO:1 and wherein said protein is antigenic and effective to elicit an immune response against *Toxoplasma gondii* oocysts in a host animal. The above vector wherein said vector is selected from the group consisting of a plasmid, bacteriophage, phage, and virus. A host cell comprising (or consisting essentially of or consisting of) the above vector. The host cell wherein said host cell is a eukaryotic cell.

A vector comprising (or consisting essentially of or consisting of) a regulatory DNA segment operably coupled to a DNA nucleotide sequence encoding a fusion protein comprising (or consisting essentially of or consisting of) one or more epitopes of rDGP5p protein wherein said rDGP5p protein comprises (or consists essentially of or consists of) an amino acid sequence shown in SEQ ID NO:1 and wherein said protein is antigenic and effective to elicit an immune response against *Toxoplasma gondii* oocysts in a host animal, operably coupled to another unrelated polypeptide sequence. The above vector, wherein the unrelated polypeptide sequence is another *Toxoplasma gondii* antigenic peptide or a *Toxoplasma* stage-specific peptide. The above vector, wherein the unrelated polypeptide sequence is carrier polypeptide or adjuvant polypeptide. The above vector wherein said vector is selected from the group consisting of a plasmid, bacteriophage, phage, and virus. A host cell comprising (or consisting essentially of or consisting of) the above vector. The host cell wherein said host cell is a eukaryotic cell.

An isolated (or recombinant) rDGP5p protein comprising (or consisting essentially of or consisting of) the amino acid sequence of SEQ ID NO: 1. The above protein wherein said protein is produced by recombinant methods. A composition comprising (or consisting essentially of or consisting of) the above protein and a pharmaceutically acceptable carrier.

An isolated (or recombinant) portion of rDGP5p protein comprising (or consisting essentially of or consisting of) one or more epitopes of rDGP5p protein wherein said rDGP5p protein comprises (or consists essentially of or consists of) an amino acid sequence shown in SEQ ID NO:1 and wherein said portion is antigenic and effective to elicit an immune response against *Toxoplasma gondii* oocysts in a host animal. The above protein wherein said protein is produced by recombinant methods. A composition comprising (or consisting essentially of or consisting of) the above protein and a pharmaceutically acceptable carrier.

A variant or derivative of the rDGP5p protein wherein said variant or derivative is antigenic and effective to elicit an immune response against Toxoplasma gondii oocysts in a host animal.

A rDGP5p fusion protein comprising (or consisting essentially of or consisting of) one or more epitopes of rDGP5p protein wherein said rDGP5p protein comprises (or consists essentially of or consists of) an amino acid sequence shown in SEQ ID NO:1 and wherein said protein is antigenic and effective to elicit an immune response against *Toxoplasma gondii* oocysts in a host animal, operably coupled to another unrelated polypeptide sequence. The above protein wherein said protein is produced by recombinant methods. A composition comprising (or consisting essentially of or consisting of) the above protein and a pharmaceutically acceptable carrier.

A vaccine composition comprising (or consisting essentially of or consisting of) an effective amount of the above protein and a pharmaceutically and/or veterinarally acceptable carrier, diluent, excipient and/or adjuvant.

A method for treating or preventing *Toxoplasma gondii* infection in a vertebrate subject comprising (or consisting essentially of or consisting of) administering to said subject the above vaccine composition in an amount effective to elicit an immune response against *Toxoplasma gondii* oocysts therein.

A method for producing hyperimmune colostrum containing antibodies which specifically and selectively bind to *Toxoplasma gondii* oocysts comprising (or consisting essentially of or consisting of) (a) administering the above protein to an animal in an amount effective to elicit an immune response against *Toxoplasma gondii* oocysts therein and (b) collecting hyperimmune colostrum containing antibodies specific for *Toxoplasma gondii* oocysts from said animal.

Hyperimmune colostrum which is generated by the above method and which contains antibodies which specifically and selectively bind to *Toxoplasma gondii* oocysts.

An isolated antibody which specifically and selectively binds one or more epitopes of rDGP5p protein (or DGP5p or DGP5p+) wherein rDGP5p protein comprises (or consists essentially of or consists of) an amino acid sequence shown in SEQ ID NO:1 and wherein said protein is antigenic and effective to elicit an immune response against *Toxoplasma gondii* oocysts. The above isolated antibody, wherein the antibody is a monoclonal antibody or a polyclonal antibody.

A method for treating or preventing toxoplasmosis in a vertebrate subject comprising (or consisting essentially of or consisting of) (a) administering an antibody specific for *Toxoplasma gondii* oocysts to the subject in an amount effective to prevent or reduce the symptoms of toxoplasmosis and, optionally, (b) determining that said subject ceases to exhibit symptoms and that treatment can be terminated.

The above method wherein the antibody is a monoclonal or polyclonal antibody or hyperimmune colostrum.

A method of identifying *Toxoplasma gondii* oocysts, said method comprising (or consisting essentially of or consisting of) contacting a test sample suspected of containing *Toxoplasma gondii* oocysts with an antibody that specifically and selectively binds rDGP5p set forth in SEQ ID NO: 1 (or DGP5p or DGP5p+) and detecting binding, wherein binding indicates the presence of *Toxoplasma gondii* oocysts. The above method wherein the antibodies are monoclonal or polyclonal. The above method wherein the antibodies are fluorescently labeled and the identification steps are carried out by means of flow cytometry.

A method of identifying *Toxoplasma gondii* oocysts antibodies in a subject, said method comprising (or consisting essentially of or consisting of) contacting a test sample suspected of containing antibodies to *Toxoplasma gondii* oocysts with an antigen wherein the antigen is rDGP5p set forth in SEQ ID NO: 1 or native Toxoplasma gondii DGP5p (or DGP5p+) and detecting antibody-antigen binding, wherein binding indicates the presence of *Toxoplasma gondii* oocysts antibodies.

A method for identifying *Toxoplasma gondii* oocyst antibodies in a subject (animal or human individual) by determining the presence of antibodies specific for *T. gondii* oocysts, said method comprising (or consisting essentially of or consisting of): (a) providing an anti-*T gondii* oocyst specific antibody or a test sample suspected of containing antibodies specific for *T. gondii* oocysts; (b) testing for a binding reaction between the test sample and native *T. gondii* oocyst protein or recombinant DGP5p antigen, rDGP5p; and (c) correlating the positive binding reaction with the presence of *T. gondii*-oocyst specific antibodies.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim

1. An isolated protein consisting of the amino acid sequence of SEQ ID NO: 1.

2. A fusion protein consisting of the amino acid sequence shown in SEQ ID NO:1 and wherein said protein is antigenic and effective to elicit an immune response against *Toxoplasma gondii* oocysts in a host animal, wherein said protein is operably coupled to another unrelated polypeptide sequence.

3. The protein according to any one of claims 1 or 2, wherein said protein is produced by recombinant methods.

4. A composition comprising the protein of any one of claims 1 or 2 and a pharmaceutically acceptable carrier.

5. A method of identifying *Toxoplasma gondii* oocysts antibodies in a subject, said method comprising contacting a test sample suspected of containing antibodies to *Toxoplasma gondii* oocysts with an antigen wherein the antigen is a protein consisting of the amino acid sequence set forth in SEQ ID NO: 1 and detecting antibody-antigen binding, wherein binding indicates the presence of *Toxoplasma gondii* oocysts antibodies; wherein said test sample is obtained from said subject.

6. The method according to claim 5, wherein said test sample is selected from the group consisting of body substances and body fluids.

7. The method according to claim 6 wherein said body substances are liquid or solid body output or tissue samples.

8. The method according to claim 7 wherein said body substances are stools.

9. The method according to claim 6, wherein said body fluids are blood, serum, saliva, or urine.

* * * * *

SEQUENCE LISTING

<160> NUMBER OF SEQ ID NOS: 9

<210> SEQ ID NO 1
<211> LENGTH: 123
<212> TYPE: PRT
<213> ORGANISM: Toxoplasma gondii

<400> SEQUENCE: 1

```
Ser Asn Lys Met Ala Ser Val Lys Arg Val Val Val Ala Val Met Ile
1               5                   10                  15

Val Asn Val Leu Ala Leu Ile Phe Val Gly Val Ala Gly Ser Thr Arg
            20                  25                  30

Asp Val Gly Ser Gly Ala Asp Asp Ser Glu Gly Ala Gly Gly Arg Glu
        35                  40                  45

Arg Gln Gln Val Gln Gln His Glu Gln Asn Glu Asp Arg Ser Leu Phe
    50                  55                  60

Glu Arg Gly Arg Ala Ala Val Thr Gly His Pro Val Arg Thr Ala Val
65                  70                  75                  80

Gly Leu Ala Ala Ala Val Val Ala Val Val Ser Leu Leu Arg Leu Leu
                85                  90                  95

Lys Arg Arg Arg Arg Ala Ile Gln Glu Glu Ser Lys Glu Ser Ala
            100                 105                 110

Thr Ala Glu Glu Glu Glu Val Ala Glu Glu Glu
        115                 120
```

<210> SEQ ID NO 2
<211> LENGTH: 369
<212> TYPE: DNA
<213> ORGANISM: Toxoplasma gondii

<400> SEQUENCE: 2

```
agtaacaaaa tggcgtctgt aaaacgcgtc gttgtggcgg taatgatcgt gaacgtgctg      60
gctttaattt ttgtgggcgt tgccggttca acgcgtgacg tagggtcagg cgcggatgac     120
tccgaaggtg ctggagggcg tgaacgacaa caggtacaac aacacgaaca aaatgaagac     180
cgatcgttat tcgaaagggg aagagcagcg gtgactggac atccagtgag gactgcagtg     240
ggacttgctg cagctgtggt ggccgttgtg tcactactgc gattgttgaa aaggaggaga     300
agacgcgcga ttcaagaaga gagcaaggag tctgcaaccg cggaagagga agaagttgcc     360
gaggaagag                                                             369
```

<210> SEQ ID NO 3
<211> LENGTH: 39
<212> TYPE: DNA
<213> ORGANISM: Toxoplasma gondii -continued

```
<400> SEQUENCE: 3
aagcagtggt atcaacgcag agtggccatt acggccggg                                39

<210> SEQ ID NO 4
<211> LENGTH: 27
<212> TYPE: DNA
<213> ORGANISM: Toxoplasma gondii

<400> SEQUENCE: 4
attctagagg ccgaggcggc cgacatg                                             27

<210> SEQ ID NO 5
<211> LENGTH: 23
<212> TYPE: DNA
<213> ORGANISM: Toxoplasma gondii

<400> SEQUENCE: 5
aagcagtggt atcaacgcag agt                                                 23

<210> SEQ ID NO 6
<211> LENGTH: 24
<212> TYPE: DNA
<213> ORGANISM: Toxoplasma gondii

<400> SEQUENCE: 6
gaattcatgg cgtctgtaaa acgc                                                24

<210> SEQ ID NO 7
<211> LENGTH: 26
<212> TYPE: DNA
<213> ORGANISM: Toxoplasma gondii

<400> SEQUENCE: 7
aagcttctta ctcttcctcg gcaact                                              26

<210> SEQ ID NO 8
<211> LENGTH: 1076
<212> TYPE: DNA
<213> ORGANISM: Toxoplasma gondii

<400> SEQUENCE: 8
gggtcgcatg actccctcag gtggttagcg gagaaacctc agatccctcg gcgcgcgacg         60
cgtgccagag cgcgggacgg ggtggcaacg agacacgttt ggataaaggt cctgccaggt        120
tgtggaatca gacgtgtggg ctgttccgcg tcggtttggt ttgtgcagag acgcactgac        180
ggttgacgtc gatcggcact cgatcctacc gtcagtcaat tttatttttgg ttttttgcaga      240 tatcatcgcg cgtgtgttca ctctaactgt gtgtatggtt cactgttttt tattgcgatt       300
ttcgtgaagt aacaaaatgg cgtctgtaaa acgcgtcgtt gtggcggtaa tgatcgtgaa       360
cgtgctggct ttaattttg tgggcgttgc cggttcaacg cgtgacgtag gtcaggcgc         420 ggatgactcc gaaggtgctg gagggcgtga acgacaacag gtacaacaac acgaacaaaa      480
tgaagaccga tcgttattcg aaaggggaag agcagcggtg actggacatc cagtgaggac       540
tgcagtggga cttgctgcag ctgtggtggc cgttgtgtca ctactgcgat tgttgaaaag       600
gaggagaaga cgcgcgattc aagaagagag caaggagtct gcaaccgcgg aagaggaaga      660
agttgccgag gaagagtaag gggcactgtg ttgctcggct cttgttgtc tcagcgtgag        720 gatttagtgc gtgtagcgca gcatgtatcg atcgatacag gcacggttgg acgtgtcgtc      780
tgtatccctt gtggcagacg gcagacgcca ttgtcagagc gtgttgcacg ttggaagaaa      840
```

```
atgtgttggt gtaatccctc gtcggacaga taccaggagg ttgcgtggtg atgatcgtgt    900
gtgcgtagag gtgtgcctcg tgataacatg aagggcaagg acctttttg tcgagcacat    960 actcaaacca gtgattgtgc gaggcgggtt gcacgcgact ttgatccatt acagttaaat   1020
atgccgaacg cgtggcctga ttcgcacaca aggcgcacag acgtaccgtt gatgag       1076

<210> SEQ ID NO 9
<211> LENGTH: 364
<212> TYPE: DNA
<213> ORGANISM: Toxoplasma gondii

<400> SEQUENCE: 9
atggcgtctg taaaacgcgt cgttgtggcg gtaatgatcg tgaacgtgct ggctttaatt     60
tttgtgggcg ttgccggttc aacgcgtgac gtagggtcag cgcgcggatga ctccgaaggt   120 gctggagggc gtgaacgaca acaggtacaa caacacgaac aaaatgaaga ccgatcgtta    180
ttcgaaaggg gaagagcagc ggtgactgga catccagtga ggactgcagt gggacttgct    240
gcagctgtgg tggccgttgt gtcactactg cgattgttga aaaggaggag aagacgcgcg    300
attcaagaag agagcaagga gtctgcaacc gcggaagagg aagaagttgc cgaggaagag    360
taag                                                                364
```